US012229951B2

(12) United States Patent
Lee et al.

(10) Patent No.: US 12,229,951 B2
(45) Date of Patent: Feb. 18, 2025

(54) METHOD FOR DIGITAL ASSAY OF TARGETS AND DEVICE USING THE SAME

(71) Applicant: KOREA ADVANCED INSTITUTE OF SCIENCE AND TECHNOLOGY, Daejeon (KR)

(72) Inventors: Kyoung Gyun Lee, Daejeon (KR); Sung Gap Im, Daejeon (KR); Seok Jae Lee, Daejeon (KR); Youn Seong Song, Daejeon (KR); Yoo Min Park, Cheongju-si (KR); Nam Ho Bae, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 559 days.

(21) Appl. No.: 17/556,971

(22) Filed: Dec. 20, 2021

(65) Prior Publication Data

US 2023/0153992 A1    May 18, 2023

(30) Foreign Application Priority Data

Nov. 18, 2021 (KR) ........................ 10-2021-0159677

(51) Int. Cl.
*G06T 7/00* (2017.01)
*G01N 21/64* (2006.01)
(Continued)

(52) U.S. Cl.
CPC ....... *G06T 7/0012* (2013.01); *G01N 21/6428* (2013.01); *G01N 33/5302* (2013.01);
(Continued)

(58) Field of Classification Search
CPC ....... G06T 7/0012; G06T 7/77; G06V 10/753; G01N 21/6428; G01N 33/5302
See application file for complete search history.

(56) References Cited

U.S. PATENT DOCUMENTS

2010/0173394 A1* 7/2010 Colston, Jr. ....... B01L 3/502715
                                                        422/68.1
2014/0221239 A1* 8/2014 Carman .......... B01L 3/502784
                                                        435/6.12
(Continued)

FOREIGN PATENT DOCUMENTS

WO    WO-2019227126 A9 *  6/2020  ........ B01L 3/502761

OTHER PUBLICATIONS

A Novel Method based on a Mask R-CNN model for processing dPCR images, XP55925606.
(Continued)

*Primary Examiner* — David Bilodeau
(74) *Attorney, Agent, or Firm* — INVENSTONE PATENT, LLC (57) ABSTRACT

Provided are a device for a digital assay of targets according to an exemplary embodiment of the present disclosure and a method using the same. The digital assay method of targets according to the exemplary embodiment of the present disclosure includes acquiring an image for a plurality of microdroplets, predicting at least one region based on the image for the plurality of microdroplets using an artificial neural network-based prediction model configured to segment at least one region among positive microdroplets, negative microdroplets, and atypical microdroplets, with the image for the plurality of microdroplets as an input, determining a number for the plurality of microdroplets based on the at least one region, and providing quantitative data of targets based on the number for the plurality of microdroplets.

16 Claims, 7 Drawing Sheets

(51) Int. Cl.
　　　*G01N 33/53*　　　(2006.01)
　　　*G06T 7/77*　　　(2017.01)
　　　*G06V 10/75*　　　(2022.01)
(52) U.S. Cl.
　　　CPC .............. *G06T 7/77* (2017.01); *G06V 10/753* (2022.01); *G06T 2207/10056* (2013.01); *G06T 2207/10064* (2013.01); *G06T 2207/20084* (2013.01); *G06T 2207/30242* (2013.01)

(56) References Cited

U.S. PATENT DOCUMENTS

| 2016/0011180 | A1* | 1/2016 | Werner | G01N 21/6486 |
| | | | | 435/288.7 |
| 2018/0100201 | A1* | 4/2018 | Garraway | C12Q 1/6886 |
| 2019/0358623 | A1* | 11/2019 | Lal | G01N 35/028 |
| 2021/0032680 | A1* | 2/2021 | Sheng | G01N 21/6428 |
| 2022/0008928 | A1* | 1/2022 | Colston, Jr. | G01N 21/645 |
| 2023/0153993 | A1* | 5/2023 | Lee | G06T 7/0012 |
| | | | | 435/6.12 |

OTHER PUBLICATIONS

A Thermosetting Oil for Droplet-Based Real-Time Monitoring of Digital PCR and Cell Culture, XP55925787.
A New Few-Shot Learning Method of Digital PCR Image Detection, XP011856869.

* cited by examiner

METHOD FOR DIGITAL ASSAY OF TARGETS AND DEVICE USING THE SAME

CROSS-REFERENCE TO RELATED APPLICATIONS

This application claims the priority of Korean Patent Application No. 10-2021-0159677 filed on Nov. 18, 2021, in the Korean Intellectual Property Office, the disclosure of which is incorporated herein by reference.

BACKGROUND

Field

The present disclosure relates to a device for a digital assay of targets and a method using the same.

Description of the Related Art

A digital assay refers to a method that segments a target into thousands of micro structures, checks a signal according to the presence/absence of the targets, and then quantifies the signal using a Poisson process. Such a digital assay has advantages of having a higher accuracy and sensitivity than the other analysis methods and enabling absolute quantification without the need for standard samples.

Examples of the digital assay method include digital polymerase chain reaction (dPCR), a digital enzyme-linked immunosorbent assay (digital ELISA), a digital proximity ligation assay (digital PLA), and a digital loop-mediated isothermal amplification assay (digital LAMP). Such digital assay methods are being applied to various diagnoses.

For example, the digital PCR is widely utilized for the purpose of research development or diagnosis in the fields of life science, genetic engineering, and medicine.

Specifically, the PCR is a molecular biology technology for replicating DNA from an isolated biological sample and can be usually used for various tasks such as diagnosis of infectious diseases, detection of hereditary diseases, identification of genetic fingerprints, gene cloning, paternity testing, genotyping identification, gene sequencing test, and DNA computing.

Specifically, the digital polymerase chain reaction (dPCR) technique is a genetic testing method which segments an existing sample into microdroplets having a volume of nanoliters and observes the fluorescence change in a target therein. Such digital PCR has a very high sensitivity and enables absolute quantitative analysis so that it has a high applicability to gene analysis, biomarker development, and gene sequencing.

In the meantime, digital assay techniques including the digital PCR have problems in that it is difficult to determine thresholds for micro-sized droplets in the photo detection and it has limitations such as optical coherence and the usage of separate fluorescence reader based on the geometric optical reader.

Accordingly, the development of a digital assay system of a new target which is capable of overcoming the limitations of the digital assay of the related art and analyzing targets in the sample with a high precision is consistently demanded.

The background of the present disclosure is described for easier understanding of the present disclosure. It should not be understood to admit the matters described in the background of the present disclosure as a prior art.

SUMMARY

As a way to overcome the limitations of the digital assay method of the related art, an adaptive threshold method has emerged. To be more specific, the adaptive threshold method is a method that segments an image and then obtains histograms for the segmented images so that it has a higher analysis accuracy than a method of collectively determining thresholds. However, according to the adaptive threshold method, an optimal threshold needs to be determined by a user for each image, which can cause user bias. Moreover, there can have still limitations in providing a result with a high reliability due to background variation, signal variation, noise spikes, and the like.

The inventors of the present disclosure have noted that image-based quantitative analysis on microdroplets can solve the above-mentioned problems.

To be more specific, the inventors of the present disclosure have attempted to develop a method which applies an artificial intelligence-based prediction model which is capable of very reliably and accurately analyzing positive and negative microstructures (microdroplets) which are randomly distributed without having a fixed unit without being user-biased, like a microdroplet-based digital assay.

Specifically, the inventors of the present disclosure have tried to apply a model capable of segmenting positive microdroplets and negative microdroplets in an image using deep learning which segments an image for microdroplets.

Moreover, the inventors of the present disclosure have noted that the microdroplets can be more accurately counted using Hough transform which finds a diameter and a radius of a circle to count the number of circles, in order to count the number of microdroplets in the segmented image.

As a result, the inventors of the present disclosure have applied the prediction model to develop a new quantitative analysis system which is capable of distinguishing and counting not only positive microdroplets, but also negative microdroplets which do not include target genes, and further atypical microdroplets which are different from microdroplets having typical shapes and sizes, in the image (for example, fluorescence image) for the microdroplets.

At this time, the inventors of the present disclosure can design a new quantitative analysis system to output an absolute quantitative value of a target gene based on the microdroplet image to enable the automatic quantitative analysis without user's intervention.

The inventors of the present disclosure have provided a new quantitative analysis system to expect that the microdroplets having a target gene can be detected with a high accuracy without being affected by factors such as atypical shape, size, low fluorescent intensity, and background variation.

More, the inventors of the present disclosure have expected that the diagnosis technical can be highly advanced.

Specifically, the inventors of the present disclosure have recognized that the signal can be analyzed with a high accuracy from the difference in the fluorescent intensities and edge ambiguity, by adjusting a focusing precision of microdroplet-based digital PCR having a limitation in analysis according to the method of the related art with artificial intelligence-based prediction model.

Therefore, an object to be achieved by the present disclosure is to provide a digital assay method of targets and a device for a digital assay of targets using the method which are configured to receive an image for microdroplets and perform the quantitative analysis on targets using an artificial neural network algorithm-based prediction model.

Objects of the present disclosure are not limited to the above-mentioned objects, and other objects, which are not mentioned above, can be clearly understood by those skilled in the art from the following descriptions.

In order to solve the above-described problems, according to an aspect of the present disclosure, a digital assay method of targets is provided.

The method includes acquiring an image for a plurality of microdroplets; predicting at least one region based on the image for the plurality of microdroplets using an artificial neural network-based prediction model configured to segment at least one region among positive microdroplets, negative microdroplets, and atypical microdroplets, with the image for the plurality of microdroplets as an input; determining a number for the plurality of microdroplets based on the at least one region, and providing quantitative data of targets based on the number for the plurality of microdroplets.

According to a feature of the present disclosure, the acquiring of an image for a plurality of microdroplets can include flowing the plurality of microdroplets to a chamber having a height which is 1.1 times to 1.9 times of a diameter of the microdroplets so that the plurality of microdroplets is present as a single layer; and acquiring a single layer image for a plurality of microdroplets. At this time, the predicting of at least one region can include predicting the at least one region based on the single layer image for the plurality of microdroplets using the prediction model.

According to another feature of the present disclosure, the at least one region includes a positive microdroplet region, a negative microdroplet region, and an atypical microdroplet region, the positive microdroplets are defined as microdroplets including the targets and fluorescent materials, the negative microdroplets are defined as microdroplets only including the fluorescent materials or void droplets, and the atypical microdroplets are defined as microdroplets which include the targets and the fluorescent materials and have a shape different from the positive microdroplets.

According to still another feature of the present disclosure, the determining of a number for the plurality of microdroplets includes: determining the number of positive microdroplets and negative microdroplets based on the positive microdroplet region and the negative microdroplet region excluding the atypical microdroplet region. Further, the providing of quantitative data of the targets further includes determining a concentration of the targets based on the number of positive microdroplets and negative microdroplets.

According to still another feature of the present disclosure, the determining of a number of positive microdroplets and negative microdroplets includes: removing the atypical microdroplet region, based on the shapes of the positive microdroplet region, the negative microdroplet region, and the atypical microdroplet region, using Hough transform; and determining a number of positive microdroplets and negative microdroplets.

According to still another feature of the present disclosure, the acquiring of an image for a plurality of microdroplets includes acquiring an image for a plurality of microdroplets consisting of a plurality of sets, and the predicting of at least one region includes: predicting at least one region for the image for the plurality of microdroplets of each of the plurality of sets, using the prediction model. Further, the providing of quantitative data of the targets includes determining a total number of copies of the targets, based on the number for the plurality of microdroplets predicted for each of the plurality of sets.

According to still another feature of the present disclosure, the predicting of at least one region can further include predicting at least one region for the plurality of microdroplets for one set selected from the plurality of sets, using the prediction model. Further, the providing of quantitative data of the targets can further include determining copy number of the targets, based on the number for the plurality of microdroplets predicted for the one set.

According to still another feature of the present disclosure, the prediction model is further configured to quantitatively analyze the targets based on the at least one region and the providing of quantitative data of the targets can further include determining quantitative data of targets based on the number for the plurality of microdroplets using the prediction model.

According to still another feature of the present disclosure, the prediction model can be further configured to segment the at least one region and a background region with the image for the plurality of microdroplets as an input. The method can further include, after the acquiring of an image, segmenting at least one region and a background region using a prediction model, determining a number for the plurality of microdroplets based on the at least one region and the background region, and providing quantitative data of targets based on the number for the plurality of microdroplets.

According to still another feature of the present disclosure, the image can be a fluorescence image.

The image is a plurality of focusing images for the plurality of microdroplets and the prediction model can be configured to further segment the at least one region with the plurality of focusing images as an input.

In order to achieve the above-described object, according to another aspect of the present disclosure, a device for a digital assay of targets is provided.

The device includes a light source which irradiates light on at least one surface of a chamber in which microdroplets including targets are disposed; an image sensor configured to provide an image for the microdroplets in the chamber; and a processor operably connected to the image sensor. At this time, the processor is configured to predict at least one region based on the image for the plurality of microdroplets using an artificial neural network-based prediction model configured to segment at least one region among positive microdroplets, negative microdroplets, and atypical microdroplets, with the image for the microdroplets as an input, determine a number for the plurality of microdroplets based on the at least one region, and determine quantitative data of the targets based on the number for the plurality of microdroplets.

According to a feature of the present disclosure, the chamber has a height which is 1.1 times to 1.9 times of a diameter of the plurality of microdroplets, and the processor is further configured to flow a plurality of microdroplets to a chamber so that the plurality of microdroplets is present as a single layer. At this time, the image sensor is further configured to acquire a single layer image for the plurality of microdroplets, and the processor can be further configured to predict the at least one region based on the single layer image for the plurality of microdroplets using the prediction model.

According to another feature of the present disclosure, the one region includes a positive microdroplet region, a negative microdroplet region, and an atypical microdroplet region, the positive microdroplets are defined as microdroplets including the targets and fluorescent materials, the negative microdroplets are defined as microdroplets only including the fluorescent materials or void droplets, and the atypical microdroplets are defined as microdroplets which include the targets and the fluorescent materials and have a shape different from the positive microdroplets.

According to still another feature of the present disclosure, the processor can be further configured to determine the number of positive microdroplets and negative microdroplets based on the positive microdroplet region and the negative microdroplet region excluding the atypical microdroplet region, and determine a concentration of the targets based on the number of positive microdroplets and negative microdroplets.

According to still another feature of the present disclosure, the processor can be further configured to remove the atypical microdroplet region, based on the shapes of the positive microdroplet region, the negative microdroplet region, and the atypical microdroplet region, using Hough transform; and determine a number of positive microdroplets and negative microdroplets.

According to still another feature of the present disclosure, the image sensor can be further configured to acquire an image for the plurality of microdroplets consisting of a plurality of sets. At this time, the processor can be further configured to predict at least one region for the image for the plurality of microdroplets of each of the plurality of sets, respectively, using the prediction model, and determine a total number of copies of the targets based on the number for the plurality of microdroplets.

According to still another feature of the present disclosure, the processor can be further configured to predict at least one region for the plurality of microdroplets for one set selected from the plurality of sets, using the prediction model, and estimate the number of copies of the targets based on the at least one region for one set.

According to still another feature of the present disclosure, the prediction model can be further configured to quantitatively analyze the targets based on the at least one region. At this time, the processor can be further configured to determine quantitative data of targets based on the number for the plurality of microdroplets using the prediction model.

According to still another feature of the present disclosure, the prediction model can be further configured to segment the at least one region and a background region with the image for the plurality of microdroplets as an input. At this time, the processor can be further configured to segment at least one region and a background region using a prediction model, determine a number for the plurality of microdroplets based on the at least one region and the background region, and provide quantitative data of the targets based on the number for the plurality of microdroplets.

Other detailed matters of the exemplary embodiments are included in the detailed description and the drawings.

The present disclosure can provide a new target quantitative system based on a microdroplet image which is capable of detecting a target in the microdroplets without including a unit for fixing the microdroplets and a unit for adjusting an interval between microdroplets.

To be more specific, according to the present disclosure, positive droplets including targets can be detected without using a unit for fixing produced microdroplets, such as an array and genes can be quantitatively analyzed with an improved accuracy.

Moreover, according to the present disclosure, targets can be detected more easily than a serial counting-based reading method in which the adjustment of intervals is essentially required as an optical signal for microdroplets which move in the channel is detected.

Specifically, according to the present disclosure, a target quantitative system configured to perform quantitative analysis based on a microdroplet image based on an artificial intelligence algorithm is provided so that it is possible to precisely quantitatively analyze the microdroplets, and moreover targets in the microdroplets.

Moreover, according to the present disclosure, from the image for microdroplets (for example, a fluorescence image), not only positive microdroplets, but also negative microdroplets which do not contain targets, and atypical microdroplets which have shapes or sizes different from those of typical microdroplets can be separately provided.

Therefore, it is possible to detect the microdroplets containing targets with a high accuracy without being affected by factors such as atypical shapes, sizes, low fluorescence intensity, and background variation.

Moreover, according to the present disclosure, a prediction model trained to segment microdroplet regions based on an image for microdroplets having various focal points is used so that even though images having ambiguous focal point are input, it is possible to segment microdroplet regions and determine quantitative data with a high accuracy.

Moreover, the present disclosure can provide an absolute quantitative value of targets based on the microdroplet image to perform automatically quantitative analysis without having user's intervention, which can contribute to high advancement of diagnostic techniques.

Specifically, according to the present disclosure, the positive signals are clearly identified to detect a very small amount of virus and easily distinguish patients with asymptomatic viral infections.

The effects according to the present disclosure are not limited to the contents exemplified above, and more various effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Advantages of the present disclosure and a method of achieving the advantages and characteristics will be clear by referring to exemplary embodiments described below in detail together with the accompanying drawings. However, the present disclosure is not limited to exemplary embodiment disclosed herein but will be implemented in various forms. The exemplary embodiments are provided by way of example only so that a person of ordinary skilled in the art can fully understand the disclosures of the present disclosure and the scope of the present disclosure. Therefore, the present disclosure will be defined only by the scope of the appended claims.

The shapes, sizes, ratios, angles, numbers, and the like illustrated in the accompanying drawings for describing the exemplary embodiments of the present disclosure are merely examples, and the present disclosure is not limited thereto. Further, in the following description, a detailed explanation of known related technologies can be omitted to avoid unnecessarily obscuring the subject matter of the present disclosure. The terms such as "including," "having," and "consist of" used herein are generally intended to allow other components to be added unless the terms are used with the term "only". Any references to singular can include plural unless expressly stated otherwise.

Components are interpreted to include an ordinary error range even if not expressly stated.

The features of various embodiments of the present disclosure can be partially or entirely bonded to or combined with each other and may be interlocked and operated in technically various ways understood by those skilled in the art, and the embodiments may be carried out independently of or in association with each other.

For clarity of interpretation of the present specification, terms used in the present specification will be defined below.

The term "target" used in the specification can be a specific DNA or RNA. Desirably, the target can be an RNA for a specific virus, but is not limited thereto.

The term "microdroplets" used in the present disclosure is microdroplets for digital PCR and can include targets (or non-target) to be amplified, a fluorescent material, or a sample for PCR.

At this time, the microdroplet can be produced by contact of a sample with oil having an immiscible property.

The term "image for microdroplet" used in the specification can refer to an image for a plurality of microdroplets which includes or does not include targets or fluorescent materials. At this time, the image for microdroplets can be a fluorescence image by microdroplets which express fluorescence by amplifying the targets, but is not limited thereto.

According to another feature of the present disclosure, the image for microdroplets may be an image having a plurality of focal points for a chamber region in which microdroplets are present.

In the meantime, the image for microdroplets may include positive microdroplets, negative microdroplets, or atypical microdroplets.

The term "positive microdroplets" used in the specification may refer to microdroplets having the target and the fluorescent material and "negative microdroplets" may refer to microdroplets only containing a fluorescent material or void droplets. Moreover, "atypical microdroplets" can refer to microdroplets having different shapes from the positive microdroplets or the negative microdroplets. To be more specific, the atypical microdroplets can refer to microdroplets which contain targets and fluorescent materials, but have a shape different from that of the positive microdroplets.

At this time, the positive microdroplets and/or the atypical microdroplets can express fluorescence by amplifying the targets.

In the meantime, according to the feature of the present disclosure, the image for microdroplets can be acquired from a chamber which contains microdroplets on which the PCR is completed. That is, the image for the microdroplets may be an image of a chamber in which the microdroplets are present.

In the meantime, a height of the chamber can be similar to a height of a channel in which a microdroplet is produced or a diameter of a microdroplet. Therefore, on the chamber, the microdroplets can be provided on a single layer.

The term "single layer image" used in the present disclosure is an image for microdroplets which are aligned on a single layer in the chamber and can refer to an image captured from an upper portion of the chamber.

At this time, the height of the chamber can be 1.1 times to 1.9 times of a diameter of the plurality of microdroplets.

The term "prediction model" used in the present disclosure can be a model trained to segment microdroplets which expression fluorescence in an image with the image for microdroplets as an input.

To be more specific, the prediction model can be a model trained to segment and classify at least one region among positive microdroplets, negative microdroplets, and atypical microdroplets or a background region in which there is no microdroplet with a fluorescence image for the microdroplets as an input.

At this time, the prediction model can be a model trained to segment a microdroplet region with a plurality of focusing images for a chamber region in which there are microdroplets as an input.

That is, when an image with an ambiguous focus is input, the prediction model can segment the microdroplet region with a high accuracy.

According to the feature of the present disclosure, the prediction model can be further trained to output quantitative data (for example, copy number or a concentration) of targets based on the segmented result.

At this time, the prediction model can be a model based on a ResNet deep neural network (DNN), but it is not limited thereto. For example, the prediction model may be a SegNet network, VGG-16, a deep convolutional neural network (DCNN), a convolutional neural network (CNN), a recurrent neural network (RNN), a restricted Boltzmann machine (RBM), a deep belief network (DBN), a single shot detector (SSD) model or a U-net-based prediction model.

Hereinafter, a device for a digital assay of targets according to various exemplary embodiments of the present disclosure and a configuration thereof will be described in detail with reference to FIG. 1.

At this time, among digital assay methods, digital PCR will be described as an example, but is not limited thereto.

Figure 1:
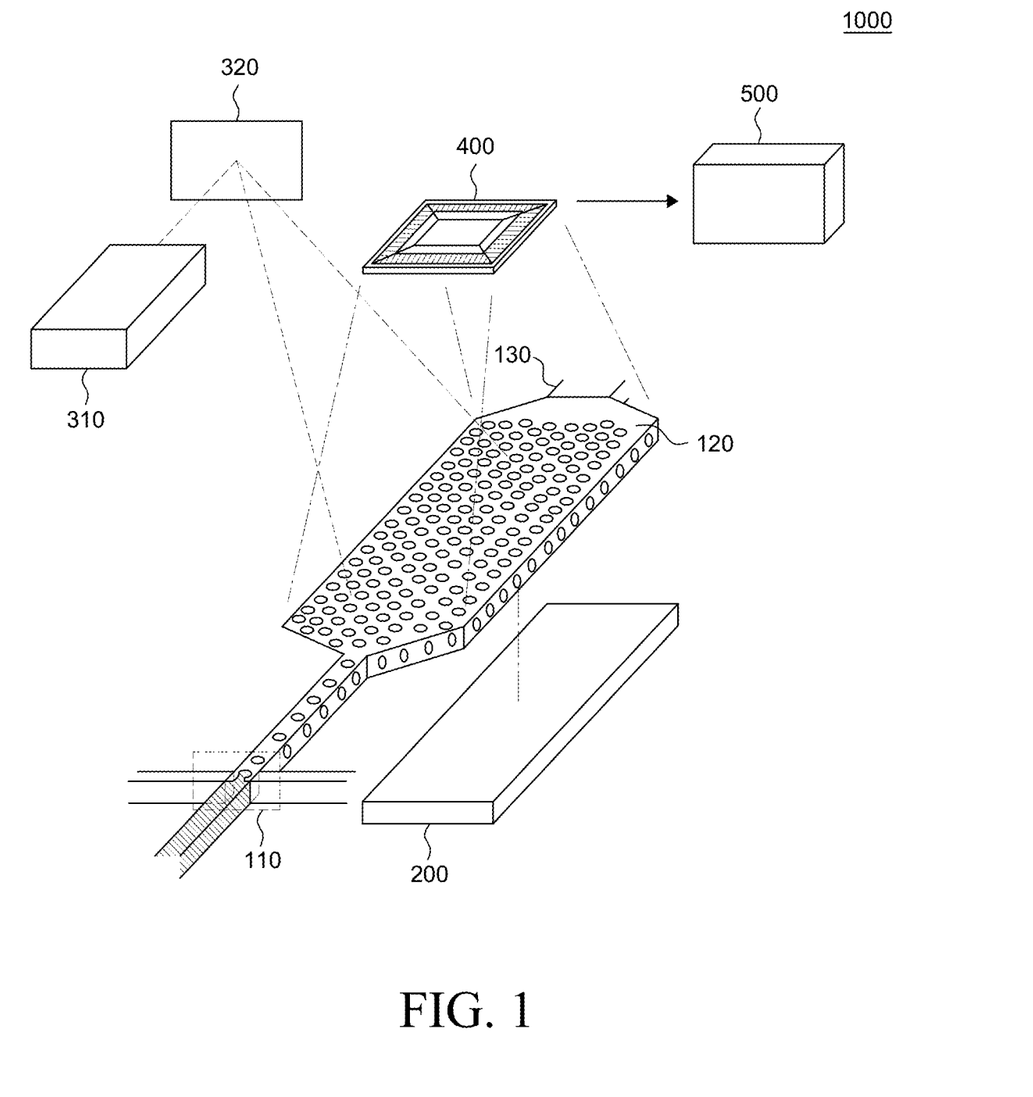
FIG. 1 illustrates a structure of a device for a digital assay of targets and configurations thereof used for various exemplary embodiments of the present disclosure.

FIG. 1 illustrates a structure of a device for a digital assay of targets and configurations thereof used for various exemplary embodiments of the present disclosure.

Referring to FIG. 1, a device 1000 for a digital assay of targets according to an exemplary embodiment of the present disclosure may be configured by a microdroplet producing unit 110 which produces microdroplets, a chamber 120 in which PCR is performed on the produced microdroplets and microdroplets on which amplification on the targets is completed is included, a valve 130 which controls the movement of the microdroplets, a light source 310, an image sensor 400 which provides an image for the microdroplets, and a processor 500 configured to communicate thereto.

At this time, the device 1000 for a digital assay of targets according to the exemplary embodiment of the present disclosure may further include a temperature adjusting unit 200 which controls a temperature of the chamber 120 and a reflector 320 which switches a direction of the light source.

To be more specific, the light is irradiated onto microdroplets on the chamber 120 by the light source 310 and the reflector 320 and images for the plurality of microdroplets in the chamber 120 may be acquired by the image sensor 400. At this time, the light source 310 may be a fluorescent lamp for expressing a color of a fluorescent material, but is not limited thereto. For example, the fluorescence may be irradiated on the chamber 120 by a fluorescence filter (not illustrated).

In the meantime, the height of the chamber 120 may be 1.1 times to 1.999 times of a diameter of the plurality of microdroplets produced from the microdroplet producing unit 110. That is, the plurality of microdroplets on the chamber 120 may be provided on a single layer.

In the meantime, the acquired image for microdroplets which is the image for the chamber including the microdroplets on which the PCR is completed may be a single layer image for microdroplets which express fluorescence.

The image for the plurality of microdroplets acquired from the image sensor 400 is transmitted to the processor 500 configured to communicate with the image sensor 400 and a digital assay of targets may be performed based on the image by the processor 500.

At this time, the processor 500 may be based on an artificial neural network-based prediction model.

To be more specific, the processor 500 may be further configured to divide types of the microdroplets in the microdroplet image, count positive microdroplets which express the targets and negative microdroplets, and determine a concentration of targets, specifically, target genes based on the counted microdroplets, by a prediction model trained to detect a region of the microdroplets with the image for the microdroplets as an input.

According to the above-described structural feature, the quantitative analysis may be possible only with the image for the microdroplets on which the PCR is completed, without adjusting a movement procedure of the microdroplets to a channel type detecting unit, and moreover adjusting an interval for the microdroplets. Specifically, the prediction model may be applied to improve the reliability of the target testing.

In the meantime, as described above, the device 1000 for a digital assay of targets according to the exemplary embodiment of the present disclosure may be applied to various digital assays other than digital PCR with configurations excluding the temperature adjusting unit 200.

Hereinafter, procedures of a digital assay method of targets using a device for a digital assay of targets according to various exemplary embodiments of the present disclosure will be described with reference to FIGS. 2A to 2C.

Figure 2A:
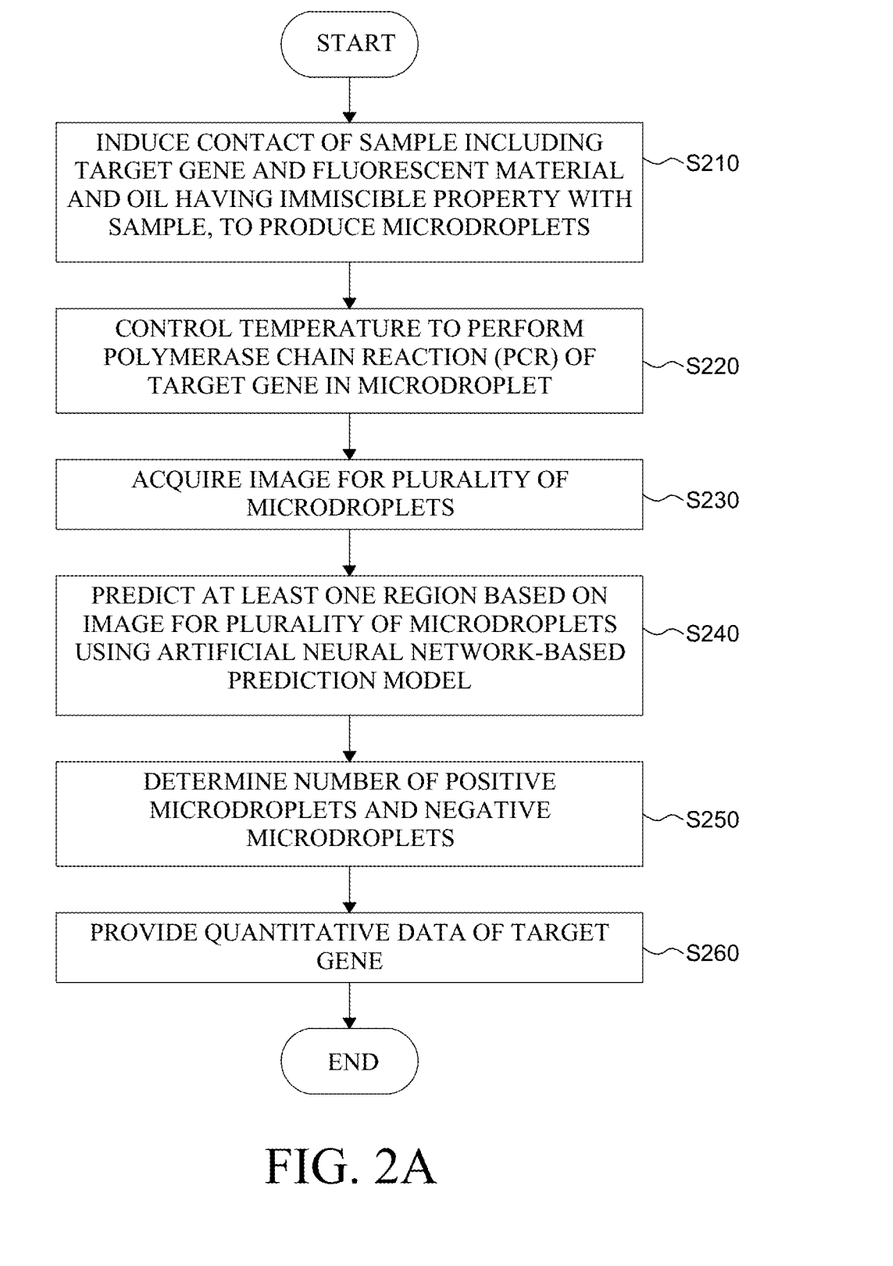
FIGS. 2A to 2C illustrate procedures of a digital assay of targets using a device for a digital assay of targets according to various exemplary embodiments of the present disclosure.
Figure 2B:
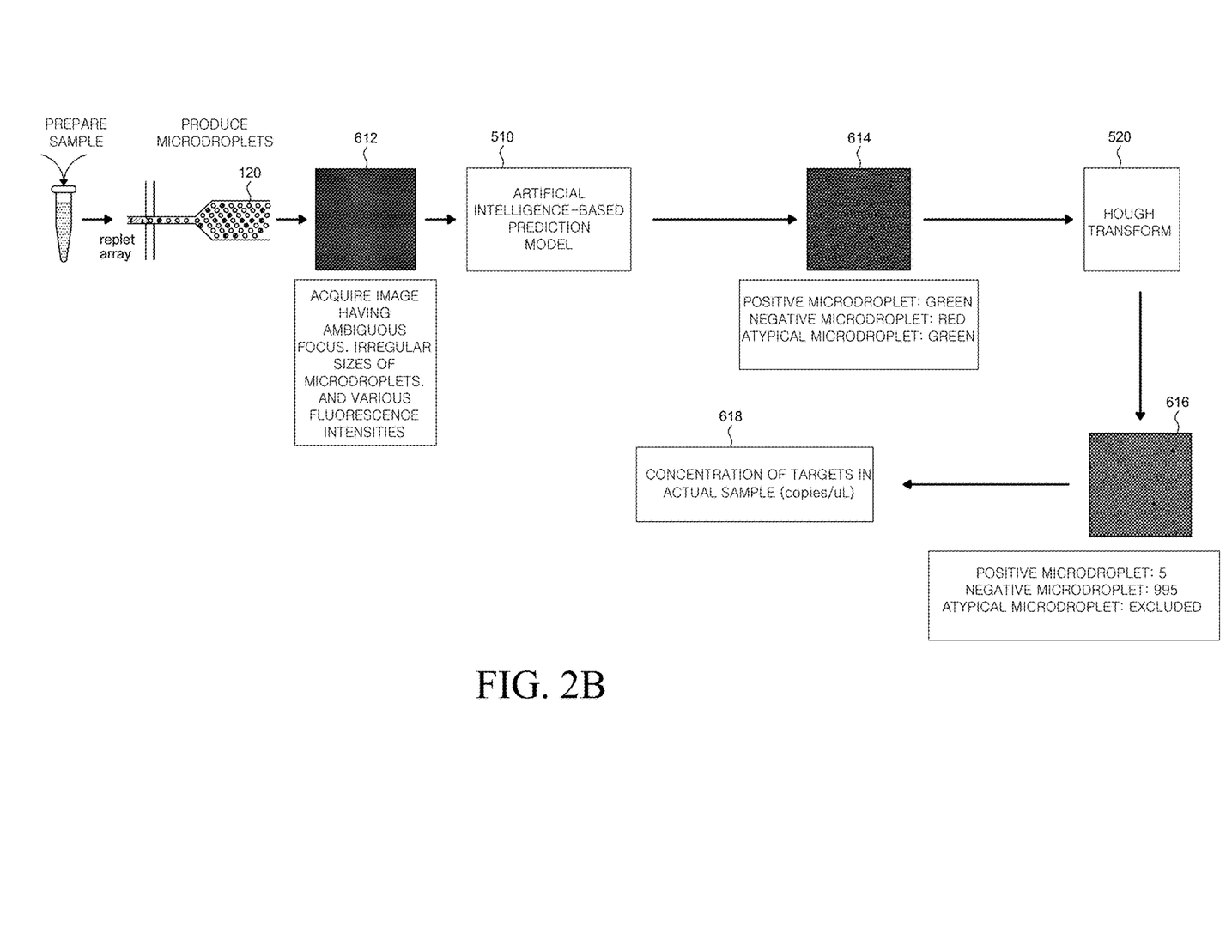
Figure 2C:
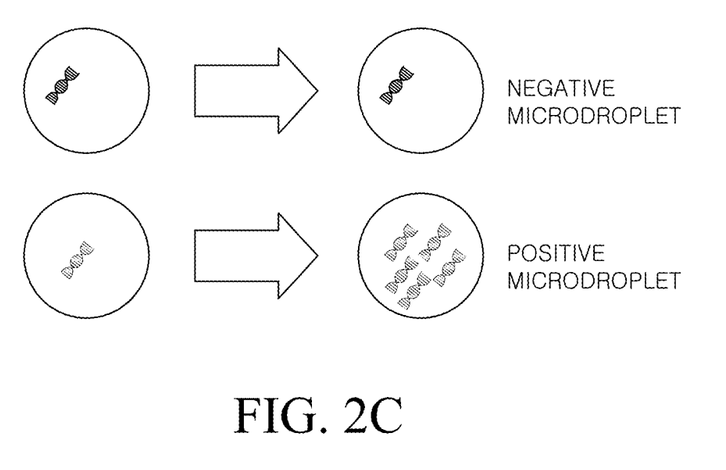

FIGS. 2A to 2C illustrate procedures of a digital assay method of targets using a device for a digital assay of targets according to various exemplary embodiments of the present disclosure.

First, referring to FIG. 2A, according to the digital assay method of targets according to an exemplary embodiment of the present disclosure, a contact of a sample and oil is induced to produce microdroplets in step S210 and a temperature is controlled for a PCR reaction for targets in the microdroplets in step S220. Next, an image for a plurality of microdroplets is acquired in step S230, at least one region of positive microdroplets, negative microdroplets, and atypical microdroplets is determined by the prediction model in step S240, and the number of positive microdroplets and negative microdroplets is determined in step S250. Finally, quantitative data for target genes is determined in step S250.

To be more specific, referring to FIG. 2B, in the step S210 of inducing the contact of the sample and oil, in the microdroplet producing unit 110, the sample including targets, fluorescent materials, moreover a primer, a polymerase is brought into contact with oil to form a plurality of microdroplets encapsulated by the oil.

As a result of the step S210 of inducing the contact of the sample and the oil, a plurality of microdroplets including targets is produced.

According to the feature of the present disclosure, after the step S210 of inducing the contact of the sample and the oil, a step of flowing the plurality of microdroplets into the chamber 120 so that the plurality of microdroplets is present as a single layer can be performed.

At this time, the height of the chamber can be 1.1 to 1.99 times of the diameter of the microdroplet, but is not limited thereto.

That is, the plurality of microdroplets can be provided on a single layer in the chamber 120.

In the meantime, the plurality of microdroplets can be at least one of positive microdroplets, negative microdroplets, and atypical microdroplets.

At this time, the positive microdroplets are defined as microdroplets including the targets and the fluorescent material, the negative microdroplets are defined as microdroplets only including the fluorescent material or void droplets, and the atypical microdroplets are defined as microdroplets having shapes different from those of the positive microdroplets or the negative microdroplets.

Next, in the step S220 of controlling a temperature, a temperature condition cycle for amplifying the targets in the microdroplets is provided and as a result, there can be microdroplets including an amplified target in the chamber 120.

To be more specific, referring to FIG. 2C together, as a result of the step S220 of controlling a temperature, the positive microdroplets including targets such as virus genes can express the fluorescence by amplifying the gene and by the fluorescent material.

In contrast, in the case of the negative microdroplets which are void microdroplets, even though the PCR is performed, the fluorescence may not be expressed.

Further, the atypical microdroplets (not illustrated) having different shapes from the negative microdroplets or the positive microdroplets may express the fluorescence or not depending on whether the target is included.

Next, referring to FIG. 2A, the image for the plurality of microdroplets on which the PCR is completed is acquired in step S230.

To be more specific, referring to FIG. 2B together, in the step S230 of acquiring the image for the plurality of microdroplets, an image 612 for the plurality of microdroplets is acquired by the quantitative analysis device 100 according to various exemplary embodiments of the present disclosure.

At this time, the image 612 for the plurality of microdroplets is a fluorescence image for a plurality of microdroplets which is present as a single layer in the chamber and may be an image which is out of focus, has irregular sizes of the microdroplets, or has various fluorescence intensities.

According to the feature of the present disclosure, in the step S230 of acquiring an image for the plurality of microdroplets, an image for a plurality of microdroplets which is formed of a plurality of sets can be acquired.

For example, in a digital PCR test to identify whether an entity is infected with a virus, copy number of the genes which are microdropletized to be amplified for absolute quantitative analysis of the target (virus) is determined. At this time, in order to acquire the image for the plurality of microdroplets and identify the number of copies per every specimen, a plurality of sets of microdroplets can be provided. Therefore, an image for the plurality of microdroplets corresponding to each of the plurality of sets can be acquired. However, it is not limited thereto, an image for a plurality of microdroplets corresponding to one set selected from the plurality of sets may also be acquired.

Next, referring to FIG. 2A, at least one region of the negative microdroplets and the atypical microdroplets can be predicted in an image for the plurality of microdroplets by the prediction model in step S240.

According to the feature of the present disclosure, in the step S240 of predicting at least one region, at least one region of the negative microdroplets and the atypical microdroplets can be predicted with respect to the image for the plurality of microdroplets corresponding to each of the plurality of sets by the prediction model.

According to another feature of the present disclosure, in the step S240 of predicting at least one region, at least one region of the positive microdroplets, the negative microdroplets and the atypical microdroplets can be predicted with respect to the image for the plurality of microdroplets corresponding to one set selected from the plurality of sets by the prediction model.

According to still another feature of the present disclosure, in the step S240 of predicting at least one region, a background region can be predicted by the prediction model together with at least one region of the negative microdroplets and the atypical microdroplets.

To be more specific, referring to FIG. 2B together, in the step S240 of predicting at least one region, the image 612 for the plurality of microdroplets is input to the artificial neural network-based prediction model 510. Next, the regions for the droplets of the positive microdroplets, the negative microdroplets, and the atypical microdroplets and the background region can be segmented to be output by the prediction model 510. At this time, referring to the image 614 in which at least one region is segmented, the negative microdroplets have red and the positive microdroplets and the atypical microdroplet including the target genes and the fluorescent material can have green by the expression of the fluorescent material. That is, even though the image 612 for the plurality of microdroplets which is out of focus, or has irregular fluorescence intensities or irregular sizes of the microdroplets is input, the prediction model 510 can segment the region for the microdroplets with a high accuracy.

In the meantime, the prediction model 510 can be based on a deep learning algorithm to segment an image based on ResNet, Segnet, Unet, faster rcnn, FCN, or Voxnet, but is not limited thereto.

Next, referring to FIG. 2A again, the step S250 of determining the number of positive microdroplets and negative microdroplets is performed.

According to the feature of the present disclosure, in the step S250 of determining the number of positive microdroplets and negative microdroplets, the atypical microdroplet region can be removed based on shapes of a positive microdroplet region, a negative microdroplet region, and an atypical microdroplet region, by Hough transform.

For example, referring to FIG. 2B together, in the region of the microdroplets segmented by the Hough transform 520, the number of positive microdroplets and negative microdroplets excluding the atypical microdroplets having an atypical shape is determined. At this time, the Hough transform 520 can determine the number of positive microdroplets and negative microdroplets by finding a diameter and a radius of the microdroplets. As a result, the number of positive microdroplets and negative microdroplets can be determined (616).

In the meantime, the number of positive microdroplets and negative microdroplets is not necessarily determined by the Hough transform.

Referring to FIG. 2A again, a step S260 of providing quantitative data of a target gene is performed.

According to the feature of the present disclosure, in the step S260 of providing quantitative data of the targets, the number of copies of the targets can be determined based on the number of positive microdroplets and negative microdroplets.

According to the feature of the present disclosure, in the step S260 of providing quantitative data of the targets, the total number of copies of the targets can be determined based on the number of positive microdroplets and negative microdroplets predicted for each of the plurality of sets.

According to still another feature of the present disclosure, in the step S260 of providing quantitative data of the targets, the total number of copies of targets per specimen (µl) is determined to determine a concentration of the targets.

For example, referring to FIG. 2B together, in the step S260 of providing quantitative data of the targets, a concentration (copies/µl) (618) of targets per specimen is determined based on the number of positive microdroplets and the number of negative microdroplets excluding the atypical microdroplets and the concentration of the targets can be provided as quantitative data.

Referring to FIG. 2A again, according to another feature of the present disclosure, in the step S260 of providing quantitative data of the targets, the number of copies of the targets can be estimated based on the number of microdroplets predicted with respect to one set selected from the plurality of sets.

For example, in the step S260 of providing quantitative data of the targets, the number of copies of the entire targets may be estimated based on the number of copies of the targets with respect to the determined one set without quantitative analysis on the entire microdroplet sets.

According to still another exemplary embodiment of the present disclosure, in the step S260 of providing quantitative data of the targets, the number of copies of targets, and further the concentration of the targets can be determined by the prediction model. That is, the prediction model can be a model trained to output quantitative analysis results (for example, the number of copies, the concentration of targets, or the number of positive microdroplets) with an image for the plurality of microdroplets as an input.

A precise analysis result for the targets can be provided by the quantitative analysis method according to various exemplary embodiments of the present disclosure as described above.

Specifically, the present disclosure can overcome the limitation of the digital assay method technique of the related art in that as the intensity of the fluorescent material for each microdroplet flowing to a detection channel is analyzed, it takes a long time to analyze, an expensive photo multiplier tube (PMT) is necessary, reproduction of the droplets can be requested, and an error in the quantitative analysis may occur due to the optical coherence.

Evaluation: Evaluation of Performance of Prediction Model According to Various Exemplary Embodiments of Present Disclosure Hereinafter, an evaluation result of a prediction model applied to various exemplary embodiments of the present disclosure will be described with reference to FIGS. 3, 4, and 5.

Figure 3A:
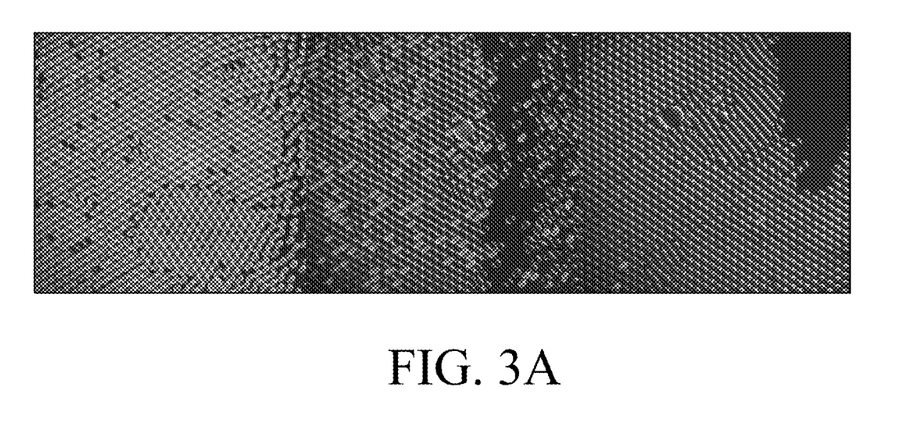
FIGS. 3A and 3B illustrate learning data of a prediction model of a device for a digital assay of targets according to various exemplary embodiments of the present disclosure.
Figure 3B:
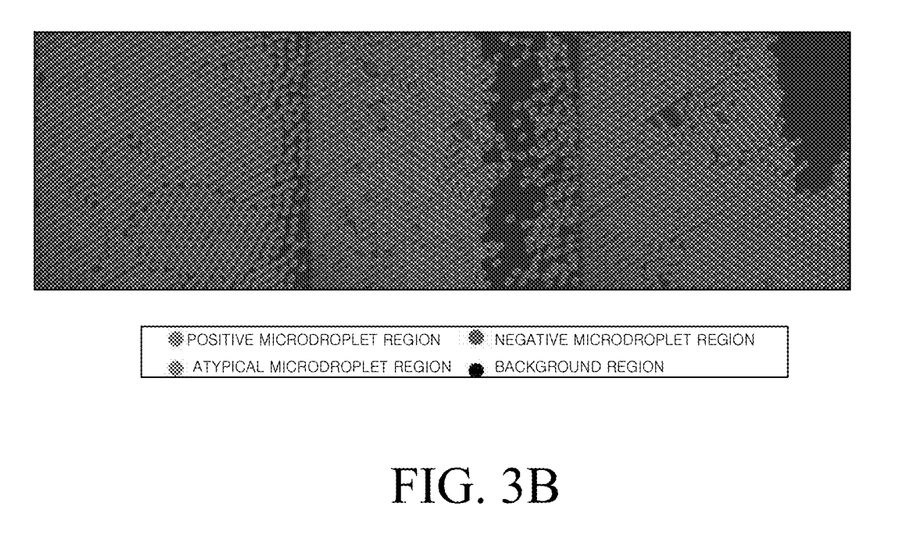
Figure 4A:
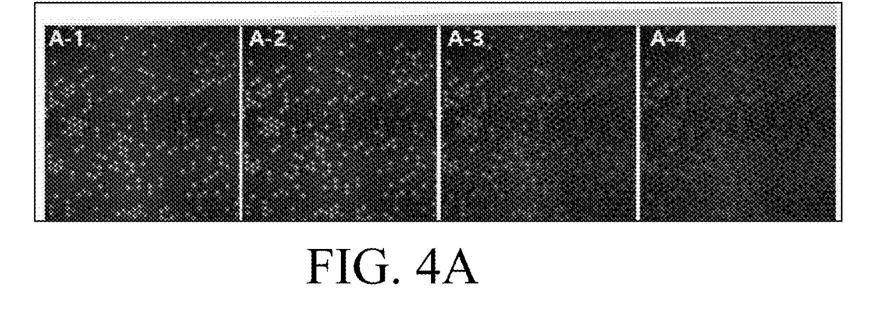
FIGS. 4A, 4B, 5A and 5B illustrate an evaluation result of a prediction model of a device for a digital assay of targets according to various exemplary embodiments of the present disclosure.
Figure 4B:
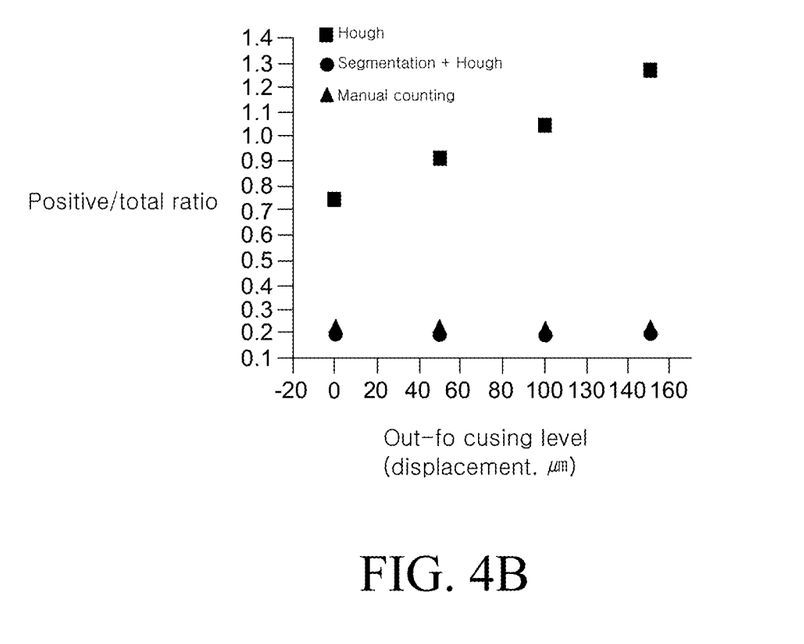
Figure 5A:
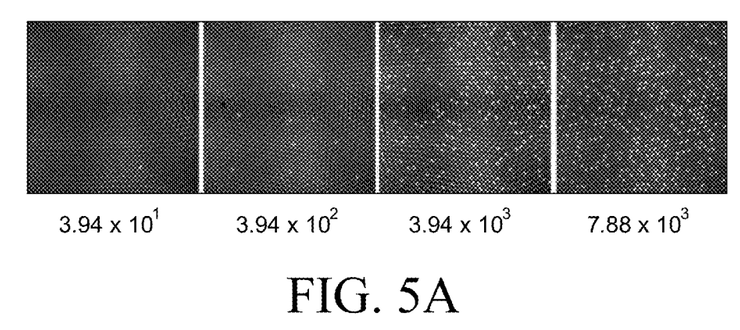
Figure 5B:
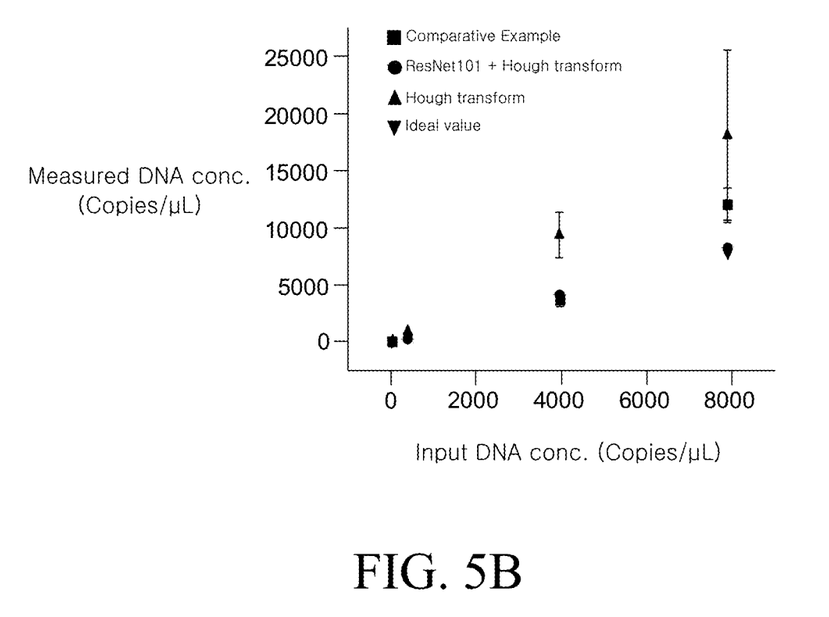

FIGS. 3A and 3B illustrate learning data of a prediction model of a device for a digital assay of targets according to various exemplary embodiments of the present disclosure. FIGS. 4, 5A and 5B illustrate an evaluation result of a prediction model of a device for a digital assay of targets according to various exemplary embodiments of the present disclosure.

First, referring to FIGS. 3A and 3B, a fluorescence image (FIG. 3A) and a masked image (FIG. 3B) used as learning data of the prediction model used for various exemplary embodiments of the present disclosure are illustrated.

To be more specific, the learning data is a fluorescence image captured in a state in which the plurality of microdroplets is spread on a single layer and can include positive microdroplets including targets and fluorescent materials and negative microdroplets which include only fluorescent materials or is void. Moreover, the fluorescence image can include atypical microdroplets having different shapes from the positive microdroplets or the negative microdroplets and also include a background region which is not microdroplets.

That is, the prediction model can be trained to segment regions for microdroplets such as a positive microdroplet region, a negative microdroplet region, and an atypical microdroplet region and further the background region, with the learning data as an input.

Moreover, the prediction model can be trained to segment regions for microdroplets such as a positive microdroplet region, a negative microdroplet region, and an atypical microdroplet region and further the background region, using a plurality of focusing images as learning data.

Therefore, even though an out-of-focused image is input, the microdroplet regions can be segmented with a high accuracy.

In the meantime, the prediction model used for various exemplary embodiments of the present disclosure can be ResNet101, but is not limited thereto.

Next, referring to FIG. 4A, a plurality of focusing images including A-1 (a focal position 0 μm), A-2 (a focal position 50 μm), A-3 (a focal position 100 μm), and A-4 (a focal position 150 μm) is illustrated.

Referring to FIG. 4B together, a prediction result on four focusing images using a combination of a prediction model and Hough transform (segmentation+Hough) used for various exemplary embodiments of the present disclosure and results of analyzing the four focusing images by only the Hough transform and manual counting by human are illustrated.

To be more specific, as the fluorescence intensity of the positive microdroplets is blurred as the out-of focus is greater, the counting results only by the Hough transform appear to deviate significantly from the manual counting values.

In contrast, the counting result using the combination of the prediction model and the Hough transform (segmentation+Hough) used for various exemplary embodiments of the present disclosure shows a high matching degree with a manual counting value even in an out-of focus.

This result can indicate an excellent segmentation performance for the prediction model trained to segment the microdroplet region, specifically, the positive microdroplet region using the plurality of focusing images as learning data.

Next, referring to FIG. 5A, fluorescence images photographed after digital PCR on an input DNA having four concentrations of $3.94 \times 10^1$ Copies/μL, $3.94 \times 10^2$ Copies/μL, $3.94 \times 10^3$ Copies/μL, and $7.88 \times 10^3$ Copies/μL are illustrated.

At this time, the higher the concentration, the more the number of positive microdroplets.

Referring to FIG. 5B, a concentration prediction result for 10 sheets of fluorescence images having four concentrations using the combination of the prediction model and the Hough transform (segmentation+Hough) used for various exemplary embodiments of the present disclosure and a concentration measuring result for 10 sheets of fluorescence images having four concentrations using a reader of Bio-Rad (Bio-Rad droplet reader) are illustrated. These results are compared with an ideal value according to the input DNA concentration.

To be more specific, when four concentrations are estimated only by the Hough transform, the result significantly deviates from the ideal value. Further, the DNA concentration estimated value using the Bio-Rad droplet reader also significantly deviates from the ideal value.

In contrast, the concentration prediction result using a combination of the prediction model and the Hough transform (ResNet 101+Hough) used for various exemplary embodiments of the present disclosure is the most approximate to the ideal value.

Such results indicate that the digital assay system of targets based on the prediction model and Hough transform configured to segment the microdroplet region, specifically, the positive microdroplet region and remove unnecessary counting information using the Hough transform can provide quantitative data of targets with a high accuracy.

That is, the digital assay method of targets based on the prediction model and/or Hough transform according to various exemplary embodiments of the present disclosure is capable of detecting positive microdroplets with a high sensitivity and providing a precise quantitative analysis result.

Specifically, according to the present disclosure, in various digital analyses, the positive microdroplets including targets can be detected without using a unit for fixing the produced microdroplets or adjusting the interval of microdroplets and the targets can be quantitatively analyzed with an improved accuracy.

Although the exemplary embodiments of the present disclosure have been described in detail with reference to the accompanying drawings, the present disclosure is not limited thereto and can be embodied in many different forms without departing from the technical concept of the present disclosure. Accordingly, the various exemplary embodiments disclosed herein are not intended to limit the technical spirit of the present invention but describe with the true scope and spirit being indicated by the following claims and the scope of the technical spirit of the present invention is not limited to the exemplary embodiments. Thus, it is to be appreciated that embodiments described above are intended to be illustrative in every sense, and not restrictive. The protective scope of the present disclosure should be construed based on the following claims, and all the technical concepts in the equivalent scope thereof should be construed as falling within the scope of the present disclosure.

[National R&D projects that supported this invention]
[Assignment unique number] 10695288
[Assignment number] 2021-DD-RD-0012
[Department name] Ministry of Science and ICT
[Research Management Professional Institution] Korea Innovation Foundation
[Research Project Name] Establishment of technology commercialization collaboration platform (nurturing R&D innovation valley)

[Research Study Name] Daedeok Innopolis Bio-Health Technology Commercialization Collaboration Platform Construction Project (1/3)
[Contribution rate] 50/100
[Organizing Agency] National Nano Fab Center
[Study period] 20210615~20211231
[National R&D projects that supported this invention]
[Assignment unique number] 1711139190
[Assignment number] NNFC-21-01
[Department name] Ministry of Science and ICT
[Research Management Professional Institution] National Nano Fab Center
[Research Project Name] Korea Advanced Institute of Science and Technology Affiliated National Nano Fab Center (R&D)—National Nano Fab Center (main project cost)
[Research Study Name] Development of contactless digital PCR that responds to the next wave (post-COVID 19) (Phase 1, 1st year)
[Contribution rate] 30/100
[Organizing Agency] National Nano Fab Center
[Study period] 20210101~20211231
[National R&D projects that supported this invention]
[Assignment unique number] 1711115958
[Assignment number] 2018R1C1B3001553
[Department name] Ministry of Science and ICT
[Research Management Professional Institution] National Research Foundation of Korea
[Research Project Name] New Researcher Project
[Research Study Name] Development of digital gene analysis technology using nano traps for catching infectious pathogens (4/4)
[Contribution rate] 20/100
[Organizing Agency] National Nano Fab Center
[Study period] 20210301~20220228

What is claimed is:

1. A method for a digital assay of targets, the method comprising:
acquiring an image for a plurality of microdroplets;
predicting regions based on the image for the plurality of microdroplets using an artificial neural network-based prediction model configured to receive the image for the plurality of microdroplets as an input and to segment regions of positive microdroplets, negative microdroplets, and atypical microdroplets, respectively, the positive microdroplets defined as microdroplets including the targets and fluorescent materials, the negative microdroplets defined as microdroplets including only the fluorescent materials or void droplets, the atypical microdroplets defined as microdroplets which include the targets and the fluorescent materials and have a shape different from the positive microdroplets;
determining a number of the positive microdroplets and the negative microdroplets based on a count of microdroplets of the positive microdroplet region and a count of microdroplets of the negative microdroplet region, while excluding the atypical microdroplet region; and
calculating a concentration of the targets based on the number of the positive microdroplets and the negative microdroplets.

2. The method according to claim 1,
wherein the acquiring of an image for a plurality of microdroplets includes:
flowing the plurality of microdroplets to a chamber having a height which is 1.1 times to 1.9 times of a diameter of the microdroplets so that the plurality of microdroplets is present as a single layer; and
acquiring a single layer image for the plurality of microdroplets, and
wherein the predicting of regions includes:
predicting the regions based on the single layer image for the plurality of microdroplets using the prediction model.

3. The method according to claim 1, wherein the determining of the number of the positive microdroplets and the negative microdroplets includes:
removing the atypical microdroplet region, based on microdroplet shapes of the positive microdroplet region, the negative microdroplet region, and the atypical microdroplet region, respectively; and
using Hough transform to determine the number of the positive microdroplets and the negative microdroplets, the Hough transform configured to find a diameter and a radius of the positive microdroplets and the negative microdroplets.

4. The method according to claim 1,
wherein the acquiring of an image for a plurality of microdroplets includes:
acquiring the image for the plurality of microdroplets consisting of a plurality of sets, and
wherein the predicting of regions includes:
predicting the regions for the image for the plurality of microdroplets of each of the plurality of sets, using the prediction model, and
wherein the providing of concentration of the targets includes:
determining a total number of copies of the targets, based on the number for the plurality of microdroplets predicted for each of the plurality of sets.

5. The method according to claim 4,
wherein the predicting of regions further includes:
predicting the regions for the plurality of microdroplets for one set selected from the plurality of sets, using the prediction model, and
wherein the providing of concentration of the targets further includes:
estimating a copy number of the targets, based on the number for the plurality of microdroplets predicted for the one set.

6. The method according to claim 1,
wherein the prediction model is further configured to quantitatively analyze the targets based on the regions and
wherein the providing of concentration of the targets includes:
determining quantitative data of the targets based on the number for the plurality of microdroplets using the prediction model.

7. The method according to claim 1,
wherein the prediction model is further configured to segment the regions and a background region with the image for the plurality of microdroplets as an input,
the method further comprising:
segmenting the regions and the background region using the prediction model,
determining the number for the plurality of microdroplets based on the regions and the background region; and
providing quantitative data of the targets based on the number for the plurality of microdroplets.

8. The method according to claim 1, wherein the image is a fluorescence image.

9. The method according to claim 1,
wherein the image is a plurality of focusing images for the plurality of microdroplets, and
wherein the prediction model is further configured to segment the regions with the plurality of focusing images as an input.

10. A device for a digital assay of targets, the device comprising:
a light source configured to irradiate light on at least one surface of a chamber in which microdroplets including targets are disposed;
an image sensor configured to provide an image for the microdroplets in the chamber; and
a processor which is operably connected to the image sensor,
wherein the processor is configured to
predict regions based on the image for the plurality of microdroplets using an artificial neural network-based prediction model configured to receive the image for the plurality of microdroplets as an input and to segment regions of positive microdroplets, negative microdroplets, and atypical microdroplets, respectively, the positive microdroplets defined as microdroplets including the targets and fluorescent materials, the negative microdroplets defined as microdroplets including only the fluorescent materials or void droplets, the atypical microdroplets defined as microdroplets which include the targets and the fluorescent materials and have a shape different from the positive microdroplets,
determine a number of the positive microdroplets and the negative microdroplets based on a count of microdroplets of the positive microdroplet region and a count of microdroplets of the negative microdroplet region, while excluding the atypical microdroplet region, and
calculate a concentration of the targets based on the number of the positive microdroplets and the negative microdroplets.

11. The device according to claim 10,
wherein the chamber has a height which is 1.1 times to 1.9 times of a diameter of the plurality of microdroplets,
wherein the processor is further configured to flow the plurality of microdroplets to the chamber so that the plurality of microdroplets is present as a single layer,
wherein the image sensor is further configured to acquire a single layer image for the plurality of microdroplets, and
wherein the processor is further configured to predict the regions based on the single layer image for the plurality of microdroplets using the prediction model.

12. The device according to claim 10, wherein the processor is further configured to
remove the atypical microdroplet region, based on microdroplet shapes of the positive microdroplet region, the negative microdroplet region, and the atypical microdroplet region, respectively; and
use Hough transform to determine the number of the positive microdroplets and the negative microdroplets, the Hough transform configured to find a diameter and a radius of the positive microdroplets and the negative microdroplets.

13. The device according to claim 10,
wherein the image sensor is further configured to acquire the image for the plurality of microdroplets consisting of a plurality of sets, and
wherein the processor is further configured to
predict the regions for the image for the plurality of microdroplets of each of the plurality of sets, using the prediction model, and
determine a total number of copies of the targets, based on the number for the plurality of microdroplets predicted for each of the plurality of sets.

14. The device according to claim 13, wherein the processor is further configured to
predict the regions for the plurality of microdroplets for one set selected from the plurality of sets, using the prediction model, and
estimate the number of copies of the targets, based on the number for the plurality of microdroplets predicted for the one set.

15. The device according to claim 10,
wherein the prediction model is further configured to quantitatively analyze the targets based on the regions and
wherein the processor is further configured to determine quantitative data of the targets based on the number for the plurality of microdroplets using the prediction model.

16. The device according to claim 10,
wherein the prediction model is further configured to segment the regions and a background region with the image for the plurality of microdroplets as an input,
wherein the processor is further configured to
segment the regions and the background region using the prediction model,
determine a number for the plurality of microdroplets based on the regions and the background region; and
provide quantitative data of the targets based on the number for the plurality of microdroplets.

* * * * *